United States Patent
Moores et al.

(10) Patent No.: US 10,412,961 B2
(45) Date of Patent: Sep. 17, 2019

(54) SUBSTITUTED 2,3-DIHYDROBENZOFURAN COMPOUNDS AND THEIR USE AS SYNERGISTS

(71) Applicants: Endura SPA, Bologna (IT); AGCHEM ACCESS LTD, Norwich, Norfolk (GB)

(72) Inventors: Graham David Moores, Stevenage (GB); Silvia Carloni, Ravenna (IT); Francesco Tozzi, Bologna (IT); Elisa Capparella, Ravenna (IT); Valerio Borzatta, Bologna (IT); János Szilágyi, Budapest (HU); László Barnabás Takács, Budapest (HU); József Schmidt, Bicske (HU); Mark Johnston, Manchester (GB)

(73) Assignees: Endura SPA, Bologna (IT); AGCHEM ACCESS LTD, Norwich, Norfolk (GB)

( * ) Notice: Subject to any disclaimer, the term of this patent is extended or adjusted under 35 U.S.C. 154(b) by 0 days.

(21) Appl. No.: 15/758,760

(22) PCT Filed: Sep. 7, 2016

(86) PCT No.: PCT/EP2016/071018
§ 371 (c)(1),
(2) Date: Mar. 9, 2018

(87) PCT Pub. No.: WO2017/042185
PCT Pub. Date: Mar. 16, 2017

(65) Prior Publication Data
US 2019/0037843 A1    Feb. 7, 2019

(30) Foreign Application Priority Data

Sep. 9, 2015  (EP) .................................... 15184406

(51) Int. Cl.
| | | |
|---|---|---|
| *A01N 43/12* | (2006.01) | |
| *C07D 311/04* | (2006.01) | |
| *A01N 25/12* | (2006.01) | |
| *A01N 25/14* | (2006.01) | |

(52) U.S. Cl.
CPC ............. *A01N 43/12* (2013.01); *A01N 25/12* (2013.01); *C07D 311/04* (2013.01); *A01N 25/14* (2013.01)

(58) Field of Classification Search
None
See application file for complete search history.

(56) References Cited

FOREIGN PATENT DOCUMENTS

| | | |
|---|---|---|
| WO | 2011020848 A1 | 2/2011 |
| WO | 2012123714 A1 | 9/2012 |

OTHER PUBLICATIONS

International Search Report and Written Opinion of PCT/EP2016/071018 dated Nov. 25, 2016.
Pap L, et al., "Comparative evaluation of new synergistics containing a butynyl-type synergophone group and piperonyl butoxide derivatives", Pest Management Science, vol. 57, No. 2, Feb. 1, 2001, pp. 186-190.

*Primary Examiner* — Mina Haghighatian
*Assistant Examiner* — Erin E Hirt
(74) *Attorney, Agent, or Firm* — Silvia Salvadori, P.C.; Silvia Salvadori

(57) ABSTRACT

The invention relates to a compound of Formula (I), wherein n is 0 or 1, $R_1$ is H or $CH_3$ and $R_2$ is a linear ($C_3$-$C_6$)alkyl and an insecticide composition comprising at least one insecticide active ingredient and at least one a compound of Formula (I).

12 Claims, No Drawings

SUBSTITUTED 2,3-DIHYDROBENZOFURAN COMPOUNDS AND THEIR USE AS SYNERGISTS

This application is a U.S. national stage of PCT/EP2016/071018 filed on 7 Sep. 2016, which claims priority to and the benefit of European Application No. 15184406.5 filed on 9 Sep. 2015, the contents of which are incorporated herein by reference in their entireties.

FIELD OF INVENTION

The invention concerns substituted 2,3-dihydrobenzofuran compounds and their uses as synergists of insecticide active ingredients.

The work leading to this invention has received funding from the European Union Seventh Framework Programme (FP7/2007-2013) under grant agreement n.605740

STATE OF THE ART

Compounds which are no toxic or only slightly toxic against insects, but in combination with active ingredients can produce a new insecticide, having an effectiveness significantly greater than the sum of the components when used separately, are named synergists.

These compounds may in principle act in several ways, but one the main mechanism is reported by interacting with the metabolism of the active substance. Metabolism can proceed through oxidative, hydrolytic, conjugative and absorption reactions and possible variations thereof.

On the basis of the discovery of synergists and of their mode of actions, a wide range research and development started from the mid 50' giving products interesting for scientific research, but only a few for market purposes.

One of the most effective and widely used synergists is represented by piperonyl butoxide (5-[2-(2-butoxyethoxy)ethoxymethyl]-6-propyl-1,3-benzodioxole) claimed in U.S. Pat. No. 2,550,737.

Piperonyl butoxide is claimed to give a synergistic effect in combination with pyrethrins as well as pyrethroids such as allethrin, prallethrin, tetramethrin and so on.

In László Pap et al., "Comparative evaluation of new synergists containing a butynyl-type synergophore group and piperonyl butoxide derivatives", Pest Management Sci., 57, 186-190, (2001) the synergistic activity of substituted methylenedioxyphenyl derivatives and substituted dimethoxybenzene derivatives is studied and the 2-butynyloxymethyl group is suggested as a synergophore group, particularly for dimethoxybenzene structure, in combination with carbofuran insecticide.

In U.S. Pat. No. 8,809,389 a composition comprising an alkynyl phenoxy compound as a synergist compound and a pesticidal active ingredient is described. This patent describes the preparation, in Example 11, of 6-(but-2-ynyloxy)-5-propyl-2,3-dihydrobenzofuran, which is not tested as synergist compound.

In Despina Phillippou et al "The interactions between piperonyl butoxide and E4, a resistance-associated esterase from the peach-potato aphid, *Myzus persicae* Sulzer (Hemiptera:Aphididae)", Pest Mang. Sci, 2013, 69(4), 499-506, 6-(but-2-ynyloxy)-2,3-dihydrobenzofuran was described (compound EN16-18) and its binding affinity was evaluated and comparable with PBO.

While these derivatives have shown synergistic activity with some active ingredients, it is still felt a great need for new synergistic compounds, that in combination with active ingredients show a better insecticide activity than the compounds of the prior art.

SUMMARY OF THE INVENTION

The above object has been achieved by a compound of Formula (I)

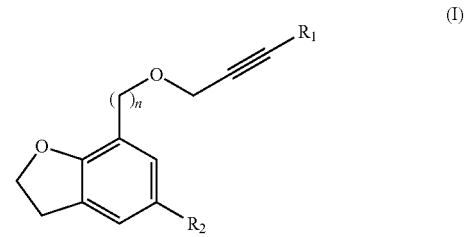

wherein n is 0 or 1,
$R_1$ is H or $CH_3$ and
$R_2$ is a linear $(C_3-C_6)$alkyl.

The inventors of the present invention surprisingly found out that an alkynyl group in the 2,3-dihydrobenzofuran structure confers synergistic activity when combined with the specific linear alkyl chain of 3-6 carbon atoms. Specifically, the selection and the positions of the two substituents in the 2,3-dihyrobenzofuran structure as per Formula (I) gave unexpected synergistic properties as it will be evident from the experimental part.

Without being bound to any theory the inventors deem that the two specific substituents in positions 5 and 7 of the 2,3-dihydrobenzofuran structure as well as the length of the alkyl chain can interact with the blockade of the enzymes, by a modulation of the binding affinity with the enzymes.

In another aspect the invention relates hence to the use of substituted 2,3-dihydrobenzofuran compounds of Formula (I) as synergistic compounds of insecticidal active ingredients.

In another aspect the invention relates to an insecticidal composition comprising at least one insecticidal active ingredient and at least one substituted 2,3-dihydrobenzofuran compound of Formula (I)

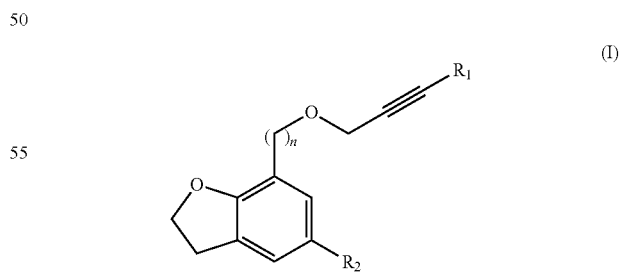

wherein n is 0 or 1,
$R_1$ is H or $CH_3$ and
$R_2$ is a linear $(C_3-C_6)$alkyl.

Under a further aspect, the invention relates to the following specific compounds:

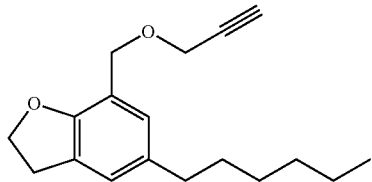 [SMILES: C#CCOCc1cc(CCCCCC)cc2c1OCC2]

5-n-hexyl-7-((prop-2-ynyloxy)methyl)-2,3-dihydrobenzofuran a compound of formula (I) wherein n is 1, $R_1$ is H, and $R_2$ is an n-hexyl substituent;

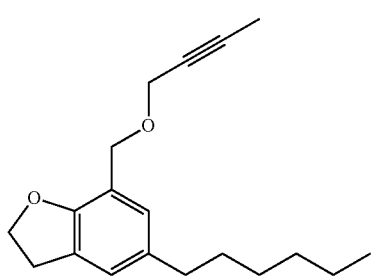 [SMILES: CC#CCOCc1cc(CCCCCC)cc2c1OCC2]

5-n-hexyl-7-((but-2-ynyloxy)methyl)-2,3-dihydrobenzofuran a compound of formula (I) wherein n is 1, $R_1$ is $CH_3$, and $R_2$ is an n-hexyl substituent;

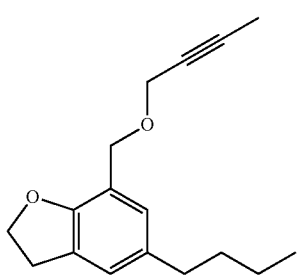 [SMILES: CC#CCOCc1cc(CCCC)cc2c1OCC2]

5-n-butyl-7-((but-2-ynyloxy)methyl)-2,3-dihydrobenzofuran a compound of formula (I) wherein n is 1, $R_1$ is $CH_3$, and $R_2$ is a butyl substituent;

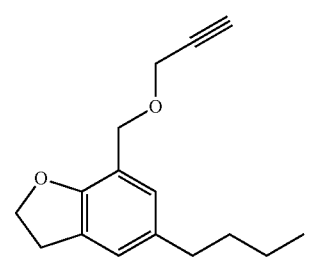 [SMILES: C#CCOCc1cc(CCCC)cc2c1OCC2]

5-n-hexyl-7-(but-2-ynyloxy)-2,3-dihydrobenzofuran, a compound of formula (I) wherein n is 0, $R_1$ is $CH_3$, and $R_2$ is an n-hexyl substituent;

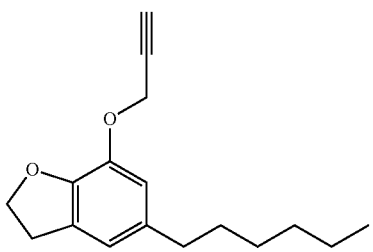 [SMILES: C#CCOc1cc(CCCCCC)cc2c1OCC2]

5-n-butyl-7-((prop-2-ynyloxy)methyl)-2,3-dihydrobenzofuran a compound of formula (I) wherein n is 1, $R_1$ is H, and $R_2$ is an n-butyl substituent;

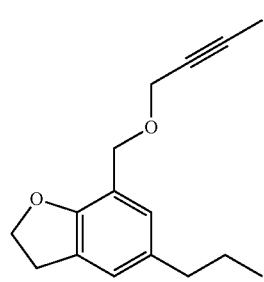

5-n-hexyl-7-(prop-2-ynyloxy)-2,3-dihydrobenzofuran a compound of formula(I) wherein n is 0, $R_1$ is H, and $R_2$ is an n-butyl substituent;

5-n-propyl-7-((but-2-ynyloxy)methyl)-2,3-dihydrobenzofuran a compound of formula (I) wherein n is 1, $R_1$ is $CH_3$, and $R_2$ is a n-propyl substituent;

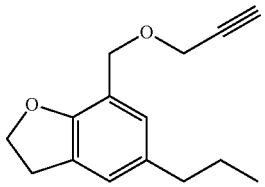

5-n-propyl-7-((prop-2-ynyloxy)methyl)-2,3-dihydrobenzofuran a compound of formula(I) wherein n is 1, $R_1$ is H, and $R_2$ is a n-propyl substituent;

In yet a further aspect of the invention, the invention relates to the use of the insecticide composition as insecticide.

In yet a further aspect of the invention, the invention relates to the insecticide composition of the invention for use in veterinary medicine.

In yet a further aspect of the invention, the invention relates to the insecticide composition for use in treating pediculosis in humans.

DETAILED DESCRIPTION OF THE INVENTION

The present invention concerns a compound of Formula (I)

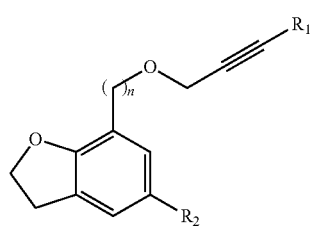

(I)

wherein n is 0 or 1,
$R_1$ is H or $CH_3$ and
$R_2$ is a linear $(C_3$-$C_6)$alkyl.

Preferably n is 1 and, more preferably $R_2$ is n-butyl or n-hexyl.

Still more preferably the compound of Formula (I) is one of:

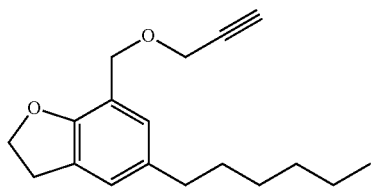

5-n-hexyl-7-((prop-2-ynyloxy)methyl)-2,3-dihydrobenzofuran), a compound of formula (I) wherein n is 1, $R_1$ is H, and $R_2$ is an n-hexyl substituent, having Chemical Formula $C_{18}H_{24}O_2$ and Molecular Weight (MW) of 272.38 Dalton whose structure is confirmed by $^1H$ and $^{13}C$ NMR analyses;

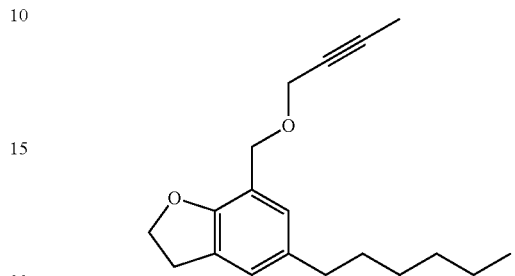

5-n-hexyl-7-((but-2-ynyloxy)methyl)-2,3-dihydrobenzofuran, a compound of formula (I) wherein n is 1, $R_1$ is $CH_3$, and $R_2$ is an n-hexyl substituent having Chemical Formula $C_{19}H_{26}O_2$ and Molecular Weight (MW) of 286.41 Dalton whose structure is confirmed by $^1H$ and $^{13}C$ NMR analyses;

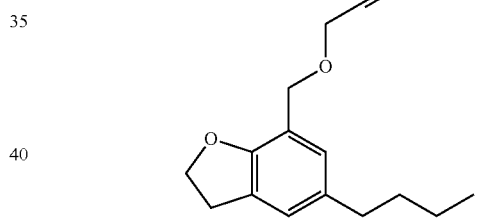

5-n-butyl-7-((but-2-ynyloxy)methyl)-2,3-dihydrobenzofuran, a compound of formula (I) wherein n is 1, $R_1$ is $CH_3$, and $R_2$ is a butyl substituent having Chemical Formula $C_{17}H_{22}O_2$ and Molecular Weight (MW) of 258.36 Dalton whose structure is confirmed by $^1H$ and $^{13}C$ NMR analyses;

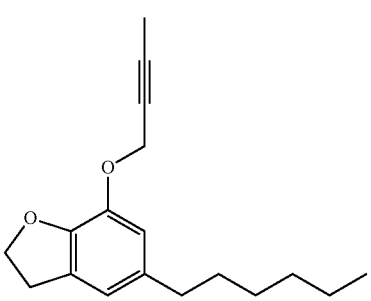 [SMILES: CC#CCOc1cc(CCCCCC)cc2c1OCC2]

5-n-hexyl-7-(but-2-ynyloxy)-2,3-dihydrobenzofuran, a compound of formula (I) wherein n is 0, $R_1$ is $CH_3$, and $R_2$ is an n-hexyl substituent having Chemical Formula $C_{18}H_{24}O_2$ and Molecular Weight (MW) of 272.38 Dalton whose structure is confirmed by $^1H$ and $^{13}C$ NMR analyses;

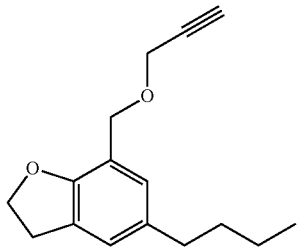 [SMILES: C#CCOCc1cc(CCCC)cc2c1OCC2]

5-n-butyl-7-((prop-2-ynyloxy)methyl)-2,3-dihydrobenzofuran, a compound of formula (I) wherein n is 1, $R_1$ is H, and $R_2$ is an n-butyl substituent having Chemical Formula $C_{16}H_{20}O_2$ and Molecular Weight (MW) of 244.33 Dalton whose structure is confirmed by $^1H$ and $^{13}C$ NMR analyses;

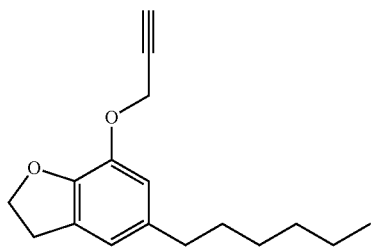

5-n-hexyl-7-(prop-2-ynyloxy)-2,3-dihydrobenzofuran, a compound of formula (I) wherein n is 0, $R_1$ is H, and $R_2$ is an n-butyl substituent having Chemical Formula $C_{17}H_{22}O_2$ and Molecular Weight (MW) of 258.36 Dalton whose structure is confirmed by $^1H$ and $^{13}C$ NMR analyses;

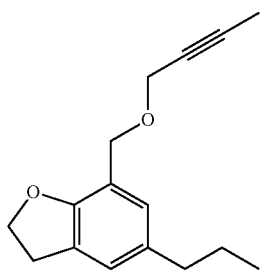 [SMILES: CC#CCOCc1cc(CCC)cc2c1OCC2]

5-n-propyl-7-((but-2-ynyloxy)methyl)-2,3-dihydrobenzofuran, a compound of formula (I) wherein n is 1, $R_1$ is $CH_3$, and $R_2$ is a n-propyl substituent having Chemical Formula $C_{16}H_{20}O_2$ and Molecular Weight (MW) of 244.33 Dalton whose structure is confirmed by $^1H$ and $^{13}C$ NMR analyses;

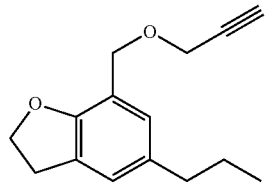 [SMILES: C#CCOCc1cc(CCC)cc2c1OCC2]

5-n-propyl-7-((prop-2-ynyloxy)methyl)-2,3-dihydrobenzofuran, a compound of formula (I) wherein n is 1, $R_1$ is H, and $R_2$ is a n-propyl substituent having Chemical Formula $C_{15}H_{18}O_2$ and Molecular Weight (MW) of 230.30 Dalton whose structure is confirmed by $^1H$ and $^{13}C$ NMR analyses.

The compound of the invention is more preferably one of:
5-n-hexyl-7-((prop-2-ynyloxy)methyl)-2,3-dihydrobenzofuran
5-n-hexyl-7-((but-2-ynyloxy)methyl)-2,3-dihydrobenzofuran
5-n-butyl-7-((but-2-ynyloxy)methyl)-2,3-dihydrobenzofuran
5-n-butyl-7-((prop-2-ynyloxy)methyl)-2,3-dihydrobenzofuran
5-n-propyl-7-((but-2-ynyloxy)methyl)-2,3-dihydrobenzofuran Still more preferably 5-n-butyl-7-((but-2-ynyloxy)methyl)-2,3-dihydrobenzofuran and 5-n-propyl-7-((but-2-ynyloxy)methyl)-2,3-dihydrobenzofuran In a further aspect the invention concerns an insecticide composition comprising at least one insecticide active ingredient and at least one compound of Formula (I)

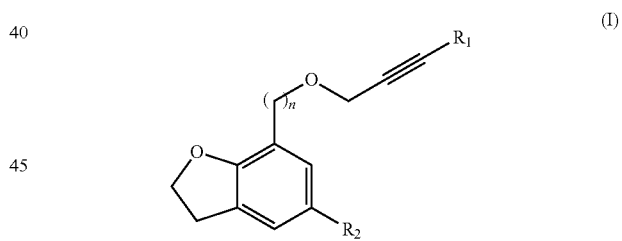

wherein n is 0 or 1,
$R_1$ is H or $CH_3$ and
$R_2$ is a linear $(C_3-C_6)$alkyl.

The preferred compounds and the preferred meaning of n, $R_1$ and $R_2$ of compounds formula (I) used in the insecticide composition of the invention are the same as stated above for compounds of Formula (I).

The compounds of the invention can be prepared by a process comprising the following steps:
a) Friedel Crafts acylation of 2,3-dihydrobenzofuran with the suitable anhydride and in the presence of a Lewis catalyst.
b) Hydrogenation of the ketone so obtained with hydrogen and in the presence of catalyst chosen between Pd/c or Pt/C.
c) Chloromethylation of the hydrogenated product coming from b) and subsequent reaction with the suitable alcohol in the presence of solid sodium hydroxide.

Specifically, following the above process the following compounds were prepared:

5-n-hexyl-7-((prop-2-ynyloxy)methyl)-2,3-dihydrobenzofuran, 5-n-hexyl-7-((but-2-ynyloxy)methyl)-2,3-dihydrobenzofuran 5-n-butyl-7-((but-2-ynyloxy)methyl)-2,3-dihydrobenzofuran 5-n-butyl 7-((prop-2-ynyloxy)methyl)-2,3-dihydrobenzofuran 5-n-propyl 7-((but-2-ynyloxy)methyl)-2,3-dihydrobenzofuran and 5-n-propyl 7-((prop-2-ynyloxy)methyl)-2,3-dihydrobenzofuran Alternatively the compounds of the invention can be prepared by a process comprising the following steps:

d) Acylation(preferably acetylation) of the intermediates as in step b);

e) Baeyer Villiger oxidation of the compound coming from d) by reaction with hydrogen peroxide to get the hydroxyl compound;

f) Etherification of the compound coming from e) in the presence of a base such as potassium carbonate and the suitable halogen alkynyl compound.

Specifically, following the above process the following compounds were prepared: 5-n-hexyl-7-(but-2-ynyloxy)-2,3-dihydrobenzofuran 5-n-hexyl-7-(prop-2-ynyloxy)-2,3-dihydrobenzofuran The position of the substituents on 2,3-dihydrobenzofuran ring was confirmed by NMR analyses, in particular by the technique of Nuclear Overhauser Effect (NOE) and gradient-selected $^1$H-$^1$H COSY (COrrelated SpectroscopY)

The insecticide composition of the present invention comprises the present compounds of the formula (I) and an insecticide active ingredient.

The ratio between the present 2,3-dihydrobenzofuran compound of the formula (I) and the insecticide active ingredient which are contained in the insecticide composition of the present invention is optionally adjustable without limitation according to the control objectives such as kinds of insects, application places, applying times, kinds of the insecticide active ingredient. Typical weight ratio of the present compound to insecticide active ingredient is from about 1:100 to about 100:1, preferably from about 1:50 to about 50:1, more preferably from 20:1 to 1:1.

Examples of the insecticide active ingredient of the present insecticide composition are:

pyrethroid compounds such as allethrin, tetramethrin, prallethrin, phenothrin, resmethrin, cyphenothrin, permethrin, cypermethrin, alpha-cypermethrin, zeta-cypermethrin, deltamethrin, tralomethrin, cyfluthrin, beta-cyfluthrin, cyhalothrin, lambda-cyhalothrin, flumethrin, imiprothrin, etofenprox, fenvalerate, esfenvalerate, fenpropathrin, silafluofen, bifenthrin, transfluthrin, flucythrinate, tau-fluvalinate, acrinathrin, tefluthrin, cycloprothrin, 2,3,5,6-tetrafluoro-4-(methoxymethyl)benzyl-(EZ)-(1RS,3RS; 1RS,3SR)-2,2-dimethyl-3-prop-1-enylcyclopropanecarboxylate, 2,3,5,6-tetrafluoro-4-methylbenzyl(EZ)-(1RS,3RS;1RS,3SR)-2,2-dimethyl-3-prop-1-enylcyclopropanecarboxylate, 2,3,5,6-tetrafluoro-4-(methoxymethyl)benzyl(1RS,3RS;1RS,3SR)-2,2-dimethyl-3-(2-methylprop-1-enyl) cyclopropanecarboxylate, empenthrin, 2,3,5,6-tetrafluoro-4-methoxymethylbenzyl(EZ)-(1RS,3RS;1RS,3SR)-3-(2-cyan-o-1-propenyl)-2,2-dimethylcyclopropanecarboxylate, 2,3,5,6-tetrafluoro-4-methoxymethylbenzyl(EZ)-(1RS,3RS;1RS,3SR)-3-(2-cyan-o-2-ethoxycarbonylvinyl)-2,2-dimethylcyclopropanecarboxylate, 2,3,5,6-tetrafluoro-4-methoxymethylbenzyl(1RS,3RS;1RS,3SR)-3-(2,2-dichlor-ovinyl)-2,2-dimethylcyclopropanecarboxylate, 2,3,5,6-tetrafluoro-4-methoxymethylbenzyl(EZ)-(1RS,3RS;1 RS,3SR)-3-methoxy-iminomethyl-2,2-dimethylcyclopropanecarboxylate and 2,3,5,6-tetrafluoro-4-methoxymethylbenzyl(EZ)-(1RS,3RS;1 RS,3SR)-3-(2-etho-xycarbonyl-2-fluorovinyl)-2,2-dimethylcyclopropanecarboxylate;

organic phosphorus compounds such as dichlorvos, fenitrothion, cyanophos, profenofos, sulprofos, phenthoate, isoxathion, tetrachlorvinphos, fenthion, chlorpyriphos, diazinon, acephate, terbufos, phorate, chlorethoxyfos, fosthiazate, ethoprophos, cadusafos and methidathion;

carbamate compounds such as propoxur, carbaryl, metoxadiazone, fenobucarb, methomyl, thiodicarb, alanycarb, benfuracarb, oxamyl, aldicarb and methiocarb; benzoylphenylurea compounds such as lufenuron, chlorfluazuron, hexaflumuron, diflubenzuron, triflumuron, teflubenzuron, flufenoxuron, fluazuron, novaluron, triazuron and bistrifluron; juvenile hormone-like substances such as pyriproxyfen, methoprene, hydroprene and fenoxycarb;

neonicotinoid compounds such as acetamiprid, nitenpyram, thiacloprid, thiamethoxam, dinotefuran, imidacloprid and clothianidin;

phenylpyrazole compounds such as acetoprole and ethiprole;

benzoylhydrazine compounds such as tebufenozide, chromafenozide, methoxyfenozide and halofenozide;

other insecticide active ingredients such as diafenthiuron, pymetrozine, flonicamid, triazamate, buprofezin, spinosad, emamectin benzoate, chlorfenapyr, indoxacarb MP, pyridalyl, cyromazine, fenpyroximate, tebufenpyrad, tolfenpyrad, pyridaben, pyrimidifen, fluacrypyrim, etoxazole, fenazaquin, acequinocyl, hexythiazox, clofentezine, fenbutatin oxide, dicofol, propargite, abamectin, milbemectin, amitraz, cartap, bensultap, thiocyclam, endosulfan, spirodiclofen, spiromesifen, amidoflumet and azadirachtin.

The insecticide composition of the present invention can also comprise a solid carrier, a liquid carrier and/or a gaseous carrier and, further, if necessary, excipients selected from a surfactant and other adjuvants to have an insecticide formulation.

The insecticide formulation can contain excipients to have an emulsion, an oil solution, a shampoo preparation, a flowable preparation, a powder, a wettable powder, a granule, a paste, a microcapsule, a foam, an aerosol, a carbon dioxide gas preparation, a tablet, a resin preparation, a paper preparation, a nonwoven fabric preparation, and a knitted or woven fabric preparation. These preparations may be used in the form of a poison bait, a insecticide coil, an electric insecticide mat, a smoking preparation, a fumigant or a sheet.

A preparation obtained with the insecticide composition of the present invention contains usually 0.01 to 98% by weight of the present composition with respect to the total weight of the preparation.

A solid carrier used for the insecticide formulation includes finely-divided powder or granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, calcium phosphate etc.), hydroxyapatite or chemical fertilizers (e.g., ammonium sulfate, ammonium phosphate, ammonium nitrate, ammonium chloride, urea, etc.); a substance which can be sublimated and is in the solid form at normal temperature (e.g., 2,4,6-triisopropyl-1,3,5-trioxane, naphthalene, p-dichlorobenzene, camphor, adamantan, etc.); wool; silk; cotton; hemp; pulp; synthetic resins (e.g., polyethylene resins such as low-density polyethylene, straight low-density polyethylene and high-density polyethylene; ethylene-vinyl ester copolymers such as ethylene-vinyl acetate copolymers; ethylene-methacrylic acid ester copolymers such as ethylene-methyl methacrylate copolymers and ethylene-ethyl methacrylate copolymers; ethylene-acrylic acid ester copolymers such as ethylene-methyl acrylate copolymers and ethylene-ethyl acrylate copolymers; ethylene-vinylcarboxylic acid copolymers such as ethylene-acrylic acid copolymers; ethylene-tetracyclododecene copolymers; polypropylene resins such as propylene homopolymers and propylene-ethylene copolymers; poly-4-methylpentene-1, polybutene-1, polybutadiene, polystyrene; acrylonitrile-styrene resins; styrene elastomers such as acrylonitrile-butadiene-styrene resins, styrene-conjugated diene block copolymers, and styrene-conjugated diene block copolymer hydrides; fluororesins; acrylic resins such as poly(methyl methacrylate); polyamide resins such as nylon 6 and nylon 66; polyester resins such as polyethylene terephthalate, polyethylene naphthalate, polybutylene terephthalate, and polycyclohexylenedimethylene terephthalate; polycarbonates, polyacetals, polyacrylsulfones, polyarylates, hydroxybenzoic acid polyesters, polyetherimides, polyester carbonates, polyphenylene ether resins, polyvinyl chloride, polyvinylidene chloride, polyurethane, and porous resins such as foamed polyurethane, foamed polypropylene, or foamed ethylene, etc.), glasses, metals, ceramics, fibers, cloths, knitted fabrics, sheets, papers, yarn, foam, porous substances, and multifilaments.

A liquid carrier includes, for example, aromatic or aliphatic hydrocarbons (e.g., xylene, toluene, alkylnaphthalene, phenylxylylethane, kerosene, gas oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, benzyl alcohol, ethylene glycol, etc.), ethers (e.g., diethyl ether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone, etc.), nitriles (e.g., acetonitrile, isobutyronitrile, etc.), sulfoxides (e.g., dimethyl sulfoxide, etc.), amides (e.g., N,N-dimethylformamide, N,N-dimethylacetamide, cyclic imides (e.g. N-methylpyrrolidone) alkylidene carbonates (e.g., propylene carbonate, etc.), vegetable oil (e.g., soybean oil, cottonseed oil, etc.), vegetable essential oils (e.g., orange oil, hyssop oil, lemon oil, etc.), and water.

A gaseous carrier includes, for example, butane gas, flon gas, liquefied petroleum gas (LPG), dimethyl ether, and carbon dioxide gas.

A surfactant includes, for example, alkyl sulfate ester salts, alkyl sulfonates, alkyl aryl sulfonates, alkyl aryl ethers and polyoxyethylenated products thereof, polyethylene glycol ethers, polyvalent alcohol esters and sugar alcohol derivatives.

Other adjuvants for formulation include binders, dispersants and stabilizers, specifically, for example, casein, gelatin, polysaccharides (e.g., starch, gum arabic, cellulose derivatives, alginic acid, etc.), lignin derivatives, bentonite, sugars, synthetic water-soluble polymers (e.g., polyvinyl alcohol, polyvinylpyrrolidone, polyacrylic acid, etc.), PAP (acidic isopropyl phosphate), BHT (2,6-di-t-butyl-4-methylphenol), BHA (a mixture of 2-t-butyl-4-methoxyphenol and 3-t-butyl-4-methoxyphenol), vegetable oils, mineral oils, fatty acids and fatty acid esters.

According to the invention the insecticide composition contain at least one 2,3-dihydrobenzofuran derivative compound as synergistic compound. Other synergists can be present in the composition, also those known in the art such as piperonyl butoxide, MGK 264 and Verbutin The present compound can be used in insect control by applying an effective amount of the present compound and a insecticide active ingredient, i.e. the present insecticide composition to insects directly and/or a biotope thereof (e.g., plants, animals, soil, etc.).

Therefore, in yet a further aspect of the invention, the invention relates to the insecticide composition of the invention for use in veterinary medicine and in yet a further aspect of the invention, the invention relates to the insecticide composition for use in treating pediculosis in humans.

When the insecticide composition of the present invention is used for controlling insects in agriculture and forestry, the application amount is usually 1 to 5,000 g/ha, preferably 10 to 800 g/ha of total amount of the present active ingredient.

When the insecticide composition of the present invention is the form of an emulsion, a wettable powder, a flowable agent, or a microcapsule, it is usually used after dilution with water so as to have the present active ingredient concentration of 0.01 to 1,000 ppm. When the insecticide composition of the present invention is the form of an oil solution, a powder or a granule, it is usually used as it is.

These preparations as it is may be sprayed as they are to plants to be protected from insects, or may be diluted with water and then sprayed to a plant to be protected from insects. Soil can be treated with these preparations to control insects living in the soil. Seedbeds before planting or planting holes or plant feet in planting can be also treated with these preparations. Further, a sheet preparation of the insecticide composition of the present invention may be applied by winding around plants, disposing in the vicinity of plants, laying on the soil surface at the plant feet or the like.

When the insecticide composition of the present invention is used for a control of insects of epidemic, the application amount is usually 0.001 to 100 mg/m$^3$ of total amount of the present active ingredient for application to space, and 0.001 to 1,000 mg/m$^2$ of total amount of the present active ingredient for application to a plane. When the insecticide composition of the present invention is the form of an emulsion, a wettable powder or a flowable agent, it is usually applied after dilution with water so as to have the present active ingredient concentration of 0.001 to 10,000 ppm, preferably 0.01 to 1,000 ppm. When the insecticide composition of the present invention is the form of an oil solution, an aerosol, a smoking preparation or a poison bait, it is usually applied as it is. The insecticide composition in the form of insecticide coil, or an electric insecticide mat is applied by emitting the present active ingredient by heating depending on its form. The insecticide composition in the form of a resin preparation, a paper preparation, a tablet, a nonwoven fabric preparation, a knitted or woven fabric preparation or a sheet preparation can be applied, for example, by leaving the preparation as it is in a space to be applied and by sending air to the preparation.

A space to which the insecticide composition of the present invention is applied for prevention of epidemics includes, for example, a closet, a Japanese-style closet, a Japanese-style chest, a cupboard, a lavatory, a bathroom, a lumber room, a living room, a dining room, a warehouse, and the car inside. The insecticide composition may be also applied in outdoor open space.

When the insecticide composition of the present invention is used for controlling parasites living outside of a livestock such as a cow, a horse, a pig, a sheep, a goat or a chicken, or a small animal such as a dog, a cat, a rat or a mouse, it can be used for said animal by a known method in the veterinary filed. Specifically, when systemic control is intended, the insecticide composition is administered, for example, as a tablet, a mixture with feed, a suppository or an injection (e.g., intramuscularly, subcutaneously, intravenously, intraperitoneally, etc.). When non-systemic control is intended, a method of using the insecticide composition of the present invention includes spraying, pour-on treatment or a spot-on treatment with the insecticide composition in the form of an oil solution or an aqueous liquid, washing an animal with the insecticide composition in the form of a shampoo preparation, and attachment of a collar or a ear tag made of the insecticide composition in the form of a resin preparation to an animal. When administered to an animal, total amount of the present active ingredient is usually in the range of 0.01 to 300 mg per 1 kg body weight of the animal.

Insects against which the insecticide composition of the present invention has controlling effect include harmful arthropods such as insects and mites. More specifically, examples thereof are listed below.

Hemiptera; Delphacidae such as *Laodelphax striatellus*, *Nilaparvata lugens*, *Sogatella furcifera* and the like; Deltocephalidae such as *Nephotettix cincticeps*, *Nephotettix virescens* and the like; Aphididae such as *Aphis gossypii*, *Myzus persicae* and the like, Pentatomidae and Alydidae, such as *Nezara antennata*, *Riptortus clavetus*, *Eysarcoris lewisi*, *Eysarcoris parvus*, *Plautia stali*, *Halyomorpha mista* and the like, Aleyrodidae such as *Trialeurodes vaporariorum*, *Bemisia argentifolii* and the like, Diaspididae, Coccidae and Margarodidae, such as *Aonidiella aurantii*, *Comstockaspis perniciosa*, *Unaspis citri*, *Ceroplastes rubens*, *Icerya purchasi* and the like, Tingidae, Cimicidae such as *Cimex lectularius* and the like, Psyllidae, and the like; Lepidoptera; Pyralidae such as *Chilo suppressalis*, *Cnaphalocrocis medinalis*, *Notarcha derogata*, *Plodia interpunctella* and the like, Noctuidae such as *Spodoptera litura*, *Pseudaletia separata*, *Trichoplusia* spp., *Heliothis* spp., *Helicoverpa* spp. and the like, Pieridae such as *Pieris rapae* and the like, Tortricidae such as *Adoxophyes* spp., *Grapholita molesta*, *Cydia pomonella* and the like, Carposinidae such as *Carposina niponensis* and the like, Lyonetiidae such as *Lyonetia* spp. and the like, Lymantriidae such as *Lymantria* spp., *Euproctis* spp. and the like, Yponomeutidae such as *Plutella xylostella* and the like, Gelechiidae such as *Pectinophora gossypiella* and the like, Arctiidae such as *Hyphantria cunea* and the like, Tineidae such as *Tinea translucens*, *Tineola bisselliella* and the like; Diptera: Culicidae such as *Culex pipiens pallens*, *Culex tritaeniorhynchus*, *Culex quinquefasciatus* and the like, *Aedes* spp. such as *Aedes aegypti*, *Aedes albopictus* and the like, *Anopheles* spp. such as *Anopheles sinensis* and the like, Chironomidae, Muscidae such as *Musca domestica*, *Muscina stabulans* and the like, Calliphoridae, Sarcophagidae, Fanniidae, Anthomyiidae such as *Delia latura*, *Delia antiqua* and the like, Tephritidae, Drosophilidae, Phoridae such as *Megaselia spiracularis* and the like, sychodidae such as *Clogmia albipunctata* and the like, Simuliidae, Tabanidae, *Stomoxys* spp., Agromyzidae, and the like; Coleoptera: rn rootworms such as *Diabrotica virgifera virgifera*, *Diabrotica undecimpunctata howardi* and the like, Scarabaeidae such as *Anomala cuprea*, *Anomala rufocuprea* and the like, Rhynchophoridae, Curculionidae and Bruchidae, such as *Sitophilus zeamais*, *Lissorhoptrus oryzophilus*, *Callosobruchus chienensis* and the like, Tenebrionidae such as *Tenebrio molitor*, *Tribolium castaneum* and the like, Chrysomelidae such as *Oulema oryzae*, *Aulacophora femoralis*, *Phyllotreta striolata*, *Leptinotarsa decemlineata* and the like, Dermestidae such as *Dermestes maculates* and the like, Anobiidae, *Epilachna* spp. such as *Epilachna vigintioctopunctata* and the like, Lyctidae, Bostrychidae, Ptinidae, Cerambycidae, *Paederus fuscipes*, and the like; Blattaria: *Blattella germanica*, *Periplaneta fuliginosa*, *Periplaneta americana*, *Periplaneta brunnea*, *Blatta orientalis* and the like; Thysanoptera: *Thrips palmi*, *Thrips tabaci*, *Frankliniella occidentalis*, *Frankliniella intonsa* and the like; Hymenoptera: Formicidae such as *Monomorium pharaosis*, *Formica fusca japonica*, *Ochetellus glaber*, *Pristomyrmex pungens*, *Pheidole noda*, and the like; Vespidae, Bethylidae, Tenthredinidae such as *Athalia japonica*, and the like; Orthoptera: Gryllotalpidae, Acrididae, and the like; Aphaniptera: *Ctenocephalides felis*, *Ctenocephalides canis*, *Pulex irritans*, *Xenopsylla cheopis*, and the like; Anoplura: *Pediculus humanus corporis*, *Phthirus pubis*, *Haematopinus eurysternus*, *Dalmalinia ovis*, and the like; Isoptera: Subterranean termites such as *Reticulitermes speratus*, *Coptotermes formosanus*, *Reticulitermes flavipes*, *Reticulitermes hesperus*, *Reticulitermes virginicus*, *Reticulitermes tibialis*, *Heterotermes aureus*, and the like, Dry wood termites such as *Incisitermes minor*, and the like, Damp wood termites such as *Zootermopsis nevadensis*, and the like; Acarina: Tetranychidae such as *Tetranychus urticae*, *Tetranychus kanzawai*, *Panonychus citri*, *Panonychus ulmi*, *Oligonychus* spp. and the like, Eriophyidae such as *Aculops pelekassi*, *Aculus schlechtendali*, and the like, Tarsonemidae such as *Polyphagotarsonemus latus*, and the like, Tenuipalpidae, Tuckerellidae, Ixodidae such as *Haemaphysalis longicornis*, *Haemaphysalis flava*, *Dermacentor variabilis*, *Ixodes ovatus*, *Ixodes persulcatus*, *Ixodes scapularis*, *Boophilus microplus*, *Amblyomma americanum*, *Rhipicephalus sanguineus*, and the like, Acaridae such as *Tyrophagus putrescentiae*, and the like, Epidermoptidae such as *Dermatophagoides farinae*, *Dermatophagoides ptrenyssnus*, and the like, Cheyletidae such as *Cheyletus eruditus*, *Cheyletus malaccensis*, *Cheyletus moorei*, *Ornithoonyssus bacoti*, *Ornithonyssus sylvairum* and the like, Dermanyssidae such as *Dermanyssus gallinae*, and the like, Trombiculidae such as *Leptotrombidium akamushi*, and the like; Araneae: *Chiracanthium japonicum*, *Latrodectus hasseltii*, and the like; Chilopoda: *Thereuonema hilgendorfi*, *Scolopendra subspinipes*, and the like; Diplopoda: *Oxidus gracilis*, *Nedyopus tambanus*, and the like; Isopoda: *Armadillidium vulgare*, and the like; Gastropoda: *Limax marginatus*, *Limax flavus*, and the like.

The insecticide composition of the present invention is preferably suitable for agriculture for professional insect control operators and for household application.

In particular the insecticide composition of the present invention is suitable for the following insect orders: Hemiptera, Diptera, Blattaria, Thysanoptera, Isoptera, and Acarina The invention will be now detailed by means of the following examples relating to the preparation of some invention synergistic compounds and to the evaluation of their activity

EXPERIMENTAL PART

Preparation of the Compounds of Formula (I)

Example 1

Synthesis of 5-n-hexyl-7-((prop-2-ynyloxy)methyl)-2,3-dihydrobenzofuran a) Synthesis of 5-n-hexyl-2,3-dihydrobenzofuran The compound was prepared following the procedure reported in U.S. Pat. No. 6,342,613 starting from 109.3 g (0.5 mol) of hexanoic anhydride (purity 98%), 120.1 g (1.0 mol) of 2,3-dihydrobenzofuran and 6.8 g (0.05 mol) of zinc chloride. The reaction was carried out at 100° C. for 4 hrs, cooled down to room temperature, washed with acidic water and the organic phase separated off. The organic phase was washed twice with water, dried on anhydrous sodium sulphate, filtered, distilled u.v (55° C./150 Pa) and subsequently at 133° C./30 Pa, obtaining 107.2 g of a yellow oil product, that was hydrogenated on Pd/C at 140° C./0.6 MPa for 7 hrs. After filtration of the catalyst, 92.9 g of an oil product was obtained whose NMR ($^1$H and $^{13}$C) and GC-MS analyses conformed to the structure $^1$H NMR (400 MHz, CDCl$_3$) d=0.86-0.90 (m, 3H, CH$_3$), 1.27-1.35 (m, 6H, 3CH$_2$), 1.52-1.60 (m, 2H, CH$_2$), 2.51 (t, J=7.81 Hz, 2H, CH$_2$), 3.15 (t, J=8.69 Hz, 2H, CH$_2$), 4.51 (t, J=8.69 Hz, 2H, CH$_2$), 6.68 (d, Jo=8.20 Hz, 1H, Ar—CH), 6.89 (d, Jo=8.20 Hz, 1H, Ar—CH), 6.99 (s br, 1H, Ar—CH).

$^{13}$C NMR (100 MHz, CDCl$_3$): d=14.06 (CH$_3$), 22.60 (CH$_2$), 28.94 (CH$_2$), 29.80 (CH$_2$), 31.73 (CH$_2$), 31.99 (CH$_2$), 35.36 (CH$_2$), 71.00 (CH$_2$), 108.75 (Ar—CH), 124.76 (Ar—CH), 126.72 (Ar—C), 127.62 (Ar—CH), 134.90 (Ar—C), 158.01 (Ar—C).

GC-MS (El) m/z (%): 204 (60) [M+], 146 (3), 133 (100), 149 (100), 115 (4), 91 (6), 77 (10).

b) Synthesis of 5-n-hexyl-7-((prop-2-ynyloxy)methyl)-2,3-dihydrobenzofuran

In a flask equipped with a stirrer 92.4 g (0.45 mol) of 5-hexyl-2,3-dihydrobenzofuran were added with 19.3 g (0.63 mol) of paraformaldehyde (purity 96.2%), 2.5 g (0.018 mol) of zinc chloride and 183 g (1.86 mol) of HCl 37%. The mixture was the heated to 70° C. and maintained under stirring for further 35 hrs. The solution was then cooled down to 30° C., added with 100 ml of toluene and the organic phase was separated off. The organic phase was then added slowly to a mixture prepared by reacting 17.4 g (0.31 mol) of propargyl alcohol and 15.6 g (0.39 mol) of solid sodium hydroxide at 60° C. for half an hour. After the addition the mixture is maintained under stirring at 60° C. for 4 hrs, cooled down to room temperature and added with 60 ml of NaCl 10% aqueous solution under stirring. The organic solution is then separated off and the solvent evaporated u.v (25° C./50 Pa). The oil residue was then distilled at 145°-150° C./50 Pa, thus obtaining 18.4 g of an oil product whose NMR ($^1$H and $^{13}$C) and GC/MS analyses conformed to the structure $^1$H NMR (400 MHz, CDCl$_3$): δ=0.88 (m, 3H, CH$_3$), 1.27-1.34 (m, 6H, 3CH$_2$), 1.56 (m, 2H, CH$_2$), 2.45 (t, J=2.34 Hz, 1H, CH), 2.52 (t, J=7.81 Hz, 2H, CH$_2$), 3.17 (t, J=8.59 Hz, 2H, CH$_2$), 4.19 (d, J=2.34 Hz, 2H, CH$_2$), 4.56 (t, J=8.59 Hz, 2H, CH$_2$), 4.57 (s, 2H, CH$_2$), 6.94 (s, 1H, Ar—CH), 6.96 (s, 1H, Ar—CH).

$^{13}$C NMR (100 MHz, CDCl$_3$): δ=14.10 (CH$_3$), 22.62 (CH$_2$), 28.99 (CH$_2$), 29.85 (CH$_2$), 31.75 (CH$_2$), 31.98 (CH$_2$), 35.37 (CH$_2$), 57.24 (CH$_2$), 66.62 (CH$_2$), 71.33 (CH$_2$), 74.42 (C), 79.90 (C), 118.25 (Ar—C), 124.65 (Ar—CH), 126.96 (Ar—C), 128.19 (Ar—CH), 135.08 (Ar—C), 156.42 (Ar—C).

GC-MS (El) m/z (%): 272 (79) [M+], 217 (24), 201 (100), 161 (23), 147 (42), 133 (12), 115 (10), 91 (10).

Example 2

Synthesis of 5-n-hexyl-7-((but-2-ynyloxy)methyl)-2,3-dihydrobenzofuran

Following the same procedure described in Example 1b), but starting from 79.6 g (0.39 mol) of 5-hexyl-2,3-dihydrobenzofuran, 19.3 g (0.63 mol) of paraformaldehyde (purity 96.2%), 2.5 g (0.018 mol) of zinc chloride and 183 g (1.86 mol) of HCl 37%, 21.7 g (0.31 mol) of 2-butyn-1-ol and 15.5 g (0.39 mol) of solid sodium hydroxide, 26.1 g of an oil product was obtained after distillation at 158-168° C./70Pa whose NMR ($^1$H and $^{13}$C) and GC/MS analyses conformed to the structure.

$^1$H NMR (400 MHz, CDCl$_3$): δ=0.88 (m, 3H, CH$_3$), 1.27-1.34 (m, 6H, 3CH$_2$), 1.56 (m, 2H, CH$_2$), 1.87 (t, J=2.34 Hz, 3H, CH$_3$), 2.52 (m, 2H, CH$_2$), 3.16 (t, J=8.59 Hz, 2H, CH$_2$), 4.15 (q, J=2.34 Hz, 2H, CH$_2$), 4.54 (s, 2H, CH$_2$), 4.55, (t, J=8.59 Hz, 2H, CH$_2$), 6.95 (s, 2H, 2Ar—CH).

$^{13}$C NMR (100 MHz, CDCl$_3$): δ=3.66 (CH$_3$), 14.09 (CH$_3$), 22.61 (CH$_2$), 29.00 (CH$_2$), 29.85 (CH$_2$), 31.75 (CH$_2$), 31.99 (CH$_2$), 35.38 (CH$_2$), 57.91 (CH$_2$), 66.49 (CH$_2$), 71.27 (CH$_2$), 75.28 (C), 82.42 (C), 118.65 (Ar—C), 124.43 (Ar—CH), 126.84 (Ar—C), 128.04 (Ar—CH), 135.01 (Ar—C)), 156.29 (Ar—C).

GC-MS (El) m/z (%): 286 (100) [M+], 231 (35), 217 (71), 201 (14), 185 (22), 161 (28), 147 (80), 133 (31), 115 (11), 91 (14).

Example 3

Synthesis of 5-n-butyl-7-((but-2-ynyloxy)methyl)-2,3-dihydrobenzofuran a) Synthesis of 5-n-butyl-2,3-dihydrobenzofuran Following the same procedure described in Example 1a), but starting from 120.1 g (1.0 mol) of 2,3-dihydrobenzofuran, 92.0 g (0.54 mol) of butyric anhydride and 7.63 g (0.056 mol) of zinc chloride 116.8 g of an oil product was obtained after distillation at 122-128° C./50 Pa. The compound was then hydrogenated on Pd/C at 140° C./0.6 MPa for 7 hrs. After filtration of the catalyst, 92.5 g of an oil product was obtained whose NMR ($^1$H and $^{13}$C) and GC-MS analyses conformed to the structure 1H NMR (400 MHz, CDCl$_3$): d=0.99 (t, J=7.42 Hz, 3H, CH3), 1.37-1.46 (tq, J1=7.81 Hz, J2=7.42 Hz, 2H, CH2), 1.60-1.66 (m, 2H, CH2), 2.60 (t, J=7.71 Hz, 2H, CH$_2$), 3.22 (t, J=8.65 Hz, 2H, CH$_2$), 4.58 (t, J=8.65 Hz, 2H, CH$_2$), 6.75 (d, Jo=8.10 Hz, 1H, Ar—CH), 6.96 (d, Jo=8.10 Hz, 1H, Ar—CH), 7.02 (s br 1H, Ar—CH).

$^{13}$C NMR (100 MHz, CDCl$_3$): d=13.91 (CH$_3$), 22.26 (CH$_2$), 29.77 (CH$_2$), 34.16 (CH$_2$), 35.01 (CH$_2$), 70.98

(CH$_2$), 108.72 (Ar—CH), 124.76 (Ar—CH), 127.71 (Ar—C), 127.62 (Ar—CH), 134.82 (Ar—C), 158.00 (Ar—C).
GC-MS (El) m/z (%): 176 (22) [M+], 133 (100)

b) Synthesis of 5-n-butyl-7-((but-2-ynyloxy)methyl)-2,3-dihydrobenzofuran

Following the same procedure of Example 2, but starting from 55.0 g (0.31 mol) of 5-n-butyl-2,3-dihydrobenzofuran, 15.0 g (0.50 mol) of paraformaldehyde (purity 96.2%) and 140 g (1.42 mol) of HCl 37%, 18.9 g (0.27 mol) of 2-butyn-1-ol and 11.8 g (0.295 mol) of solid sodium hydroxide, 34.5 g of an oil product was obtained after distillation at 134°-138° C./20 Pa, whose NMR ($^1$H and $^{13}$C) and GC/MS analyses conformed to the structure $^1$H NMR (400 MHz, CDCl$_3$): δ=0.92 (t, J=7.42 Hz, 3H, CH$_3$), 1.34 (tq, J$_1$=7.81 Hz, J$_2$=7.42 Hz, 2H, CH$_2$), 1.55 (m, 2H, CH$_2$), 1.86 (t, J=2.34 Hz, 3H, CH$_3$), 2.52 (t, J=7.81 Hz, 2H, CH$_2$), 3.16 (t, J=8.59 Hz, 2H, CH$_2$), 4.15 (q, J=2.34 Hz, 2H, CH$_2$), 4.54 (s, 2H, CH$_2$), 4.55 (t, J=8.59 Hz, 2H, CH$_2$), 6.95 (s, 2H, Ar—CH).

$^{13}$C NMR (100 MHz, CDCl$_3$): δ=3.60 (CH$_3$), 13.91 (CH$_3$), 22,29 (CH$_2$), 29.80 (CH$_2$), 34.12 (CH$_2$), 34.99 (CH$_2$), 57.87 (CH$_2$), 66.43 (CH$_2$), 71,21 (CH$_2$), 75.23 (C), 82.36 (C), 118.60 (Ar—C), 124.39 (Ar—CH), 126.78 (Ar—C), 127.99 (Ar—CH), 134.89 (Ar—C), 156.23 (Ar—C).

GC-MS (El) m/z (%): 258 (100) [M+], 215 (44), 189 (85), 161 (37), 147 (92), 133 (38).

Example 4

Synthesis of 5-n-hexyl-7-(but-2-ynyloxy)-2,3-dihydrobenzofuran a) Synthesis of 5-n-hexyl-7-acetyl-2,3-dihydrobenzofuran

A mixture of 455.1 g (2.23 mol) of the compound of Example 1a), (143.0 g) 1.40 mol) of acetic anhydride and 19.1 g (0.14 mol) of zinc chloride was heated to 100° C. under stirring for 7 hrs. The mixture was then added with further 143.0 g (1.4 mol) of acetic anhydride and 19.1 g (0.14 mol) of zinc chloride. The mixture was stirred at 100° C. for further 5 hrs, cooled down to room temperature and added with 200 ml of diisopropyl ether and 200 ml of an aqueous solution of HCl (1.4 M). The organic phase was separated off, washed with water and dried on anhydrous sodium sulphate. After filtration, the organic phase was distilled u.v. at 30° C./180Pa and at 143°-145° C./30 Pa, thus obtaining 310 g of a thick oil, whose NMR ($^1$H and $^{13}$C) and GC-MS analyses conformed to the structure.

$^1$H NMR (400 MHz, CDCl$_3$): δ=0.86-0.89 (m, 3H, CH$_3$), 1.27-1.33 (m, 6H, 3CH$_2$), 1.53-1.60 (m, 2H, CH$_2$), 2.54 (t, J=7.76 Hz; 2H, CH$_2$), 2.60 (s, 3H, CH$_3$), 3.20 (t, J=8.73 Hz; 2H, CH$_2$), 4.66 (t, J=8.73 Hz; 2H, CH$_2$), 7.17 (s br, 1H, Ar—CH), 7.48 (s br, 1H, Ar—CH).

$^{13}$C NMR (100 MHz, CDCl$_3$): δ=14.01 (CH$_3$), 22.52 (CH$_2$),28.83 (CH$_2$), 29.02 (CH$_2$), 30.86 (CH$_3$), 31.63 (CH$_2$), 31.66 (CH$_2$), 35.06(CH$_2$), 71.86 (CH$_2$), 120.12 (Ar—C), 127.20 (Ar—CH), 129.13 (Ar—C), 129.84 (Ar—CH), 134.94 (Ar—C), 158.62 (Ar—C), 197.17 (C=O).

GC-MS (El) m/z (%): 246 (30) [M+], 231 (20), 175 (100), 157 (12)

b) Synthesis of 5-n-hexyl-7-hydroxy-2,3-dihydrobenzofuran

A mixture of 104.3 g (0.42 mol) of 5-n-hexyl-7-acetyl-2,3-dihydrobenzofuran,80 g (1.715 mo) of formic acid and 200 ml of dichloromethane was heated to 40° C. under stirring. 125.0 g (1.287 mol) of an aqueous solution of hydrogen peroxide 35% was then added slowly, maintaining an addition speed of 0.6 ml/min.

The solution was then stirred at 40° C. for further 3 hrs and then added again with 50 g (0.51 mol) of an aqueous solution of hydrogen peroxide 35%.

The mixture was maintained at 40° C. under stirring for further 7 hrs, cooled to room temperature and the organic phase was separated and evaporated u.v (20° C./500Pa). 140.2 g of an oil compound was obtained that was mixed with 166 ml of sodium hydroxide aqueous solution (3M), 15 ml of methanol and 50 ml of water. The mixture was heated to 45° C. for 4 hrs, cooled to 20° C. and the solid product filtered and after crystallization from diisopropyl ether, obtaining 76.3 g of a white solid whose NMR ($^1$H and $^{13}$C) and GC-MS analyses conformed to the structure.

$^1$H NMR (400 MHz, CDCl$_3$): d=0.88-0.91 (m, 3H, CH$_3$), 1.28-1.34 (m, 6H, 3CH$_2$), 1.53-1.60 (m, 2H, CH$_2$), 2.50 (t, J=7.81 Hz, 2H, CH$_2$), 3,21 (t, J=8.59 Hz, 2H, CH$_2$), 4.60 (t, J=8.59 Hz, 2H, CH$_2$), 5.26 (s br, 1H, OH), 6.58 (s, 1H, Ar—CH), 6.60 (s, 1H, Ar—CH).

$^{13}$C NMR (100 MHz, CDCl$_3$): d=14.07 (CH$_3$), 22.59 (CH$_2$), 28.92 (CH$_2$), 30.52 (CH$_2$), 31.72 (CH$_2$), 31.84 (CH$_2$), 35.49 (CH$_2$), 71.93 (CH$_2$), 114.85 (Ar—CH), 116.52 (Ar—CH), 127.60 (Ar—C), 136.64 (Ar—C), 139.75 (Ar—C), 144.51 (Ar—C).

GC-MS (El) m/z (%): 220 (66) [M+], 203 (1), 149 (100), 136 (2), 91(8), 77 (10).

c) Synthesis of 5-n-hexyl-7-(but-2-ynyloxy)-2,3-dihydrobenzofuran

A mixture of 20.1 g (0.091 mol) of 5-n-hexyl-7-hydroxy-2,3-dihydrobenzofuran, 12.8 g (0.091 mol) of anhydrous potassium carbonate, 100 ml of acetone and 11.31 g (0.085 mol) of 1-bromo-2-butyne was heated to reflux for 10 hrs. The mixture was the cooled down to room temperature, filtered and the organic solution evaporated u.v (25° C./500 Pa). 25.3 g of an oil product was obtained whose NMR ($^1$H and $^{13}$C) and GC/MS analyses conformed to the structure.

$^1$H NMR (400 MHz, CDCl$_3$): δ=0.88-0.91 (m, 3H, CH$_3$), 1,28-1.35 (m, 6H, 3CH$_2$), 1.54-1.62 (m, 2H, CH$_2$), 1.83 (t, J=2.34 Hz, 3H, CH$_3$), 2.53 (m, 2H, CH$_2$), 3.16 (t, J=8.59 Hz, 2H, CH$_2$), 4.56 (t, J=8.59 Hz, 2H, CH$_2$), 4.69 (q, J=2.34 Hz, 2H, CH$_2$), 6.67 (s, 2H, Ar—CH).

$^{13}$C NMR (100 MHz, CDCl$_3$): δ=3.42 (CH$_3$), 13.89 (CH$_3$), 22.42 (CH$_2$), 28.70 (CH$_2$), 30.09 (CH$_2$), 31.58 (CH$_2$), 31.73 (CH$_2$), 35.47 (CH$_2$), 57.16 (CH$_2$), 71.44 (CH$_2$), 74.17 (C), 83.33), 113.86 (Ar—CH), 117.52 (Ar—CH), 128.05 (Ar—C), 135.56 (Ar—C), 141.79 (Ar—C), 146.56 (Ar—C).

GC-MS (El) m/z (%): 272 (100) [M+], 219 (30), 201 (60), 187 (20), 149 (100), 121 (9), 91 (19).

Example 5

Synthesis of 5-n-butyl-7-((prop-2-ynyloxy)methyl)-2,3-dihydrobenzofuran

Following the procedure of Example 3b), but starting from 50.7 g (0.288 mol) of 5-n-butyl-2,3-dihydrobenzofuran, 15.0 g (0.5 mol) of paraformaldehyde, 140 g (1.42 mol) of HCl 37%, 14.9.0 g (0.265 mol) of propargyl alcohol and 11.8 g (0.295 mol) of solid sodium hydroxide, 24.5 g of an oil product is obtained after distillation at 124°-131° C./15 Pa whose NMR ($^1$H and $^{13}$C) and GC/MS analyses conformed to the structure $^1$H NMR (400 MHz, CDCl$_3$): δ=0.93 (t, J=7.42 Hz, 3H, CH$_3$), 1.36 (tq, J$_1$=7.81 Hz, J$_2$=7.42 Hz, 2H, CH$_2$), 1.57 (m, 2H, CH$_2$), 2.47 (t, J=2.34 Hz, 1H, CH$_3$), 2.54 (t, J=7.81 Hz, 2H, CH$_2$), 3.18 (t, J=8.59 Hz, 2H, CH$_2$), 4.21 (d, J=2.34 Hz, 2H, CH$_2$), 4.57 (t, J=8.59 Hz, 2H, CH$_2$), 4.58 (s, 2H, CH$_2$), 6.96 (s, 1H, Ar—CH), 6.97 (s, 1H, Ar—CH).

$^{13}$C NMR (100 MHz, CDCl$_3$): δ=13.88 (CH$_3$), 22.24 (CH$_2$), 29.75 (CH$_2$), 34.07 (CH$_2$), 34.94 (CH$_2$), 57.14 (CH$_2$), 66.50 (CH$_2$), 71.21 (CH$_2$), 74.36 (CH), 79.79 (C), 118.16 (Ar—C), 124.55 (Ar—CH), 126.85 (Ar—C), 128.07 (Ar—CH), 134.89 (Ar—C), 156.30 (Ar—C).

GC-MS (EN 16-43/1) (EI) m/z (%): 244 (69) [M+], 201 (100), 189 (31), 161 (27), 147 (44), 133 (13), 151 (12), 91 (12).

Example 6

Synthesis of
5-n-hexyl-7-(prop-2-ynyloxy)-2,3-dihydrobenzofuran

Following the procedure of Example 4c), a mixture of 20.1 g (0.091 mol) of 5-n-hexyl-7-hydroxy-2,3-dihydrobenzofuran, 12.8 g (0.093 mol) of anhydrous potassium carbonate, 100 ml of acetone and 11.1 g (0.093 mol) of propargyl bromide was heated to reflux for 10 hrs. The mixture was the cooled down to room temperature, filtered and the organic solution evaporated u.v (25° C./500 Pa). 24.2 g of an oil product was obtained whose NMR ($^1$H and $^{13}$C) and GC/MS analyses conformed to the structure.

$^1$H NMR (400 MHz, CDCl$_3$): δ=0.86-0.90 (m, 3H, CH$_3$), 1.27-1.34 (m, 6H, 3CH$_2$), 1.57 (m, 2H, CH$_2$), 2.47 (t, J=2.54 Hz, 1H, CH), 2.52 (m, 2H, CH$_2$), 3.16 (t, J=8.59 Hz, 2H, CH$_2$), 4.57 (t, J=8.59 Hz, 2H, CH$_2$), 4.74 (d, J=2.54 Hz, 2H, CH$_2$), 6.67 (s, 1H, Ar—CH), 6.68 (s, 1H, Ar—CH).

$^{13}$C NMR (100 MHz, CDCl$_3$): δ=14.00 (CH$_3$), 22.53 (CH$_2$), 28.81 (CH$_2$), 30.17 (CH$_2$), 31.65 (CH$_2$), 31.77 (CH$_2$), 35.53 (CH$_2$), 56.79 (CH$_2$), 71.64 (CH$_2$), 75.32 (CH), 78.78 (C), 114.43 (Ar—CH), 118.11 (Ar—CH), 128.41 (Ar—C), 135.77 (Ar—C), 141.51 (Ar—C), 146.74 (Ar—C).

GC-MS (EI) m/z(%): 258 (100) [M+], 219 (48), 187 (37), 173 (18), 159 (17), 149 (100), 91 (27), 77 (10).

Example 7

Synthesis of 5-n-propyl-7-((but-2-ynyloxy)methyl)-2,3-dihydrobenzofuran a) Synthesis of 5-n-propyl-2,3-dihydrobenzofuran Following the procedure of Example 1a), a mixture of 58.7 g (0.45 mol) of propionic anhydride, 100.0 g (0.83 mol) of 2,3-dihydrobenzofuran and 6.2 g (0.045 mol) of zinc chloride was heated at 100° C. for 2 hrs under stirring, cooled down to room temperature, washed with acidic water and the organic phase separated off. The organic phase was washed twice with water, dried on anhydrous sodium sulphate, filtered, distilled u.v (30° C./150 Pa) and then at 109°-112° C./40 Pa, obtaining 66.8 g of a colorless oil product, that was hydrogenated on Pd/C at 140° C./0.6MPa for 7 hrs. After filtration of the catalyst, 63.2 g of an oil product is obtained whose NMR ($^1$H and $^{13}$C) and GC-MS analyses conformed to the structure.

$^1$H NMR (400 MHz, CDCl$_3$)): δ=0.88-0.93 (m, 3H, CH$_3$), 1.51-1.57 (m, 2H, CH$_2$), 2.49 (t, J=8 Hz, 2H, CH$_2$), 3.14 (t, J=8 Hz, 2H, CH$_2$), 4.51 (m, 2H, CH$_2$), 6.92 (s 1H, Ar—CH), 6.95 (s 1H, Ar—CH).

$^{13}$C NMR (100 MHz, CDCl$_3$) δ=13.59 (CH$_3$), 19.06 (CH$_2$), 24.79 (CH$_2$), 119.01 (Ar—C), 124.03 (Ar—CH), 126.47 (Ar—C), 127.67 (Ar—CH), 134.43 (Ar—C), 155.96 (Ar—C).

GC-MS (EI) m/z (%): 162 (50) [M+], 133 (100), 91 (5), 77 (10)

b) Synthesis of 5-n-propyl-7-((but-2-ynyloxy) methyl)-2,3-dihydrobenzofuran

Following the procedure of Example 1b) 45.3 g (0.28 mol) of 5-n-propyl-2,3-dihydrobenzofuran were added with 15.0 g (0.50 mol) of paraformaldehyde (purity 96.2%) and 140 g (1.42 mol) of HCl 37%.The mixture was then heated to 60° C. and maintained under stirring for further 6 hrs. The solution was then cooled down to 30° C., added with 50 ml of diisopropyl ether and the organic phase was separated off. The organic phase was then added slowly to a mixture prepared by reacting 17.6 g (0.25 mol) of 2-butyn-1-ol and 11.3 g (0.28 mol) of solid sodium hydroxide at 60° C. for half an hour. After the addition the mixture is maintained under stirring at 60° C. for 10 hrs, cooled down to room temperature and added with 60 ml of NaCl 10% aqueous solution under stirring. The organic solution is then separated off and the solvent evaporated u.v (25° C./500 Pa). The oil residue was then distilled at 131°-134° C./10 Pa obtaining 29.7 g of an oil product whose NMR ($^1$H and $^{13}$C) and GC/MS analyses conform to the structure $^1$H NMR (400 MHz, CDCl$_3$) (EN 16-46/2): δ=0.92 (t, 3H, J=7.42 Hz, CH$_3$(12)), 1.59 (tq, J$_1$=7.81 Hz, J$_2$=7.42 Hz, 2H, CH$_2$(11)), 1.85 (t, J=2.34 Hz, 3H, CH$_3$(18)), 2.50 (m, 2H, CH$_2$(10)), 3.14 (t, J=8.59 Hz, 2H, CH$_2$(7)), 4.14 (q, J=2.34 Hz, 2H, CH$_2$(15)), 4.53 (s, 2H, CH$_2$(13)), 4.53 (t, J =8.59 Hz, 2H, CH$_2$(8)), 6.94 (s, 2H, Ar—CH(4, 6)).

$^{13}$C NMR (100 MHz, CDCl$_3$) (EN 16-46/2): δ=3.44 (CH$_3$(18)), 13.63 (CH$_3$(12)), 24.84 (CH$_2$(11)), 29.66 (CH$_2$), 37.29 (CH$_2$), 57.72 (CH$_2$(15)), 66.28 (CH$_2$(13)), 71.08 (CH$_2$(8)), 75.13 (C(17)), 82.21 (C(16)), 118.47 (Ar—C(5)), 124.30 (Ar—CH), 126.64 (Ar—C(3)), 127.91 (Ar—CH), 134.50 (Ar—C(1)), 156.16 (Ar—C(2)).

GC-MS (EN 16-46/1) (EI) m/z (%): 244 (93) [M+], 215 (42), 189 (35), 175 (100), 161 (43), 147 (85), 133 (37), 115 (16), 91 (21).

Example 8

Synthesis of 5-n-propyl-7-((prop-2-ynyloxy) methyl)-2,3-dihydrobenzofuran

Following the same procedure described in Example 7b), but starting from 45.3 g (0.28 mol) of 5-n-propyl-2,3-dihydrobenzofuran, 15.0 g (0.50 mol) of paraformaldehyde (purity 96.2%) and 140 g (1.42 mol) of HCl 37%, 15.7 g (0.28 mol) of propargyl alcohol and 11.3 g (0.28 mol) of solid sodium hydroxide, 28.2 g of an oil product was obtained after distillation at 117°-120° C./20 Pa, whose NMR ($^1$H and $^{13}$C) and GC/MS analyses conformed to the structure.

$^1$H NMR (400 MHz, CDCl$_3$) (EN 16-47/4): δ=0.92 (t, 3H, J=7.42 Hz, CH$_3$(12)), 1.59 (tq, J$_1$=7.81 Hz, J$_2$=7.42 Hz, 2H, CH$_2$(11)), 2.44 (t, J=2.34 Hz, 1H, CH$_3$(17)), 2.50 (m, 2H, CH$_2$(10)), 3.15 (t, J=8.59 Hz, 2H, CH$_2$(7)), 4.18 (d, J=2.34

Hz, 2H, CH$_2$(15)), 4.54 (t, J=8.59 Hz, 2H, CH$_2$(8)), 4.56 (s, 2H, CH$_2$(13)), 6.94 (s, 1H, Ar—CH), 6.95 (s, 1H, Ar—CH).

$^{13}$C NMR (100 MHz, CDCl$_3$) (EN 16-47/4): δ=13.67 (CH$_3$(12)), 24.87 (CH$_2$(11)), 29.69 (CH$_2$), 37.31 (CH$_2$), 57.07 (CH$_2$(15)), 66.44 (CH$_2$(13)), 71.15 (CH$_2$(8)), 74.33 (CH(17)), 79.74 (C(16)), 118.10 (Ar—C(5)), 124.55 (Ar—CH), 126.79 (Ar—C(3)), 128.08 (Ar—CH), 134.60 (Ar—C(1)), 156.30 (Ar—C(2)).

GC-MS (EN 16-47/1) (EI) m/z (%): 230 (76) [M+], 201 (100), 190 (6), 175 (40), 161 (32), 147 (46), 133 (15), 115 (15), 91 (15).

Example 9

Inhibition of Oxidase Enzymes by the Synergists in *Bemisia tabaci*

Ability of the compounds of the invention to inhibit oxidative enzymes (P450), a major mechanism conferring resistance to xenobiotics, was measured using recombinant enzymes corresponding to CYPCM1 from *Bemisia tabaci*.

The following synergists were tested in comparison with piperonyl butoxide (PBO):

CYP6CM1

Substrate used was 7-ethoxycoumarin for inhibition assays as described by Ulrich and Weber (1972) and adapted to microplate format as described by De Sousa et al. (1995). This method had successfully been used previously to characterise inhibition by some piperonyl butoxide analogues against microsomal preparations from whole insects (Moores et al. 2009)

For inhibition assays, stock solutions of the compounds of Examples 1-9 (10 mM) were prepared in acetone. Diluted recombinant enzyme (50 μL) was mixed with 3 μL of the above mentioned compound stock solutions, with acetone only used as a control. After 10 min incubation at room temperature, 80 μL of 0.125 mM 7- ethoxycoumarin was added, followed by 10 μL 9.6 mM NADPH (nicotinamide adenine dinucleotide phosphate) in 0.1 M sodium phosphate, pH 7.8, and O-deethylation activity monitored as above. A PBO solution (10 mM) was prepared in the same way as a comparison.

The results are reported in the Table 1 below:

TABLE 1

*Bemisia tabaci* CYPCM1 percentage of activity remaining

| Compound | % activity remaining | sem |
|---|---|---|
| Compound of Example 2 | 27.49 | 1.77 |
| Compound of Example 3 | 3.16 | 1.85 |
| Compound of Example 4 | 39.22 | 2.12 |
| Compound of Example 5 | 87.62 | 4.76 |
| Compound of Example 6 | 61.16 | 4.61 |
| Compound of Example 7 | 17.92 | 1.06 |
| Compound of Example 8 | 86.22 | 4.10 |
| PBO | 106.49 | 4.50 |

The compounds of Examples 2-8 therefore show an inhibition activity better than PBO being the percentage of the remaining activity of the enzyme less when the synergists of the invention were used instead of using PBO.

Example 10

Inhibition of Esterasenzymes by Synergists in *Myzus persicae*

Inhibition of esterase activity cannot be measured by simple colourimetric assays using routine model substrates, as the synergist does not bind at the active site (Philippou et al., 2013). It was envisaged, therefore, that the 'esterase intereference assay' (Khot et al., 2008) would be utilised for the purified esterases from aphids. Various esterase substrates were assessed to find one suitable of monitoring inhibition in an insect homogenate. The Myzus persicae resistance associated esterase, FE4, was used.

FE4

Initially the esterase interference assay was carried out, as being the 'absolute' protocol for characterizing interactions between the compounds of Example 1-9 and FE4. However, since this is a protracted method, a selection of products already reported in the literature were used to compare the interference assay and the use of a model substrate.

From the literature (Philippou et al., 2013) it is known that 1-naphthyl acetate is not suitable for this assay. Instead, 4-nitrophenyl acetate was used. A 10 mM pNA stock was prepared in acetone and added to 0.02 M phosphate buffer pH 7.0 (final concentration 2 mM). The comparison was made with 6 PBO analogues of variable efficacy.

The result of this relatively high-throughput method was found to rank the products identically to the interference assay, so this method was used for further analysis of FE4 interactions.

For the assay 10 μL of purified FE4 was diluted to a total volume of 50 μL by the addition of 0.02 M phosphate buffer, pH 7.0 in individual wells of a microplate (maxisorb, NUNC). To each well, 2.5 μL of 10 mM of the compound of Example 1 and of Example 2 in acetone was added and incubated for 10 mins, with acetone only used as a control. Following incubation, 100 μL of 0.02 phosphate buffer, pH 7.0 and 100 μL of 2 mM 4-nitrophenyl acetate was added (final volume in well 250 μL, final substrate concentration 0.8 mM). Enzyme activity was read at 405 nm in a Spectramax Tmax for 5 min, with readings taken every 5 secs. The rate (mOD min$^{-1}$) was calculated by the integrated software, Softmax Pro v.5.4. A PBO solution (10 mM) was prepared in the same way as a comparison.

The results of the percentage of the activity remaining are reported in the Table 2 below.

TABLE 2

FE4 *Myzus persicae* esterases percentage of activity remaining

| Compound | % activity remaining | sem |
|---|---|---|
| Compound of Example 1 | 26.16 | 0.45 |
| Compound of Example 2 | 35.44 | 1.00 |
| Compound of Example 3 | 19.85 | 0.58 |
| Compound of Example 4 | 23.97 | 0.21 |
| Compound of Example 5 | 18.38 | 0.62 |
| Compound of Example 6 | 29.8 | 0.70 |
| Compound of Example 7 | 19.91 | 0.69 |
| Compound of Example 8 | 23.93 | 1.15 |
| PBO | 45.78 | 1.52 |

The compounds of Examples 1-8 therefore show an inhibition activity better than PBO being the percentage of the remaining activity of the enzyme less when the synergists of the invention were used instead of using PBO.

The invention claimed is:

1. A compound of Formula (I)

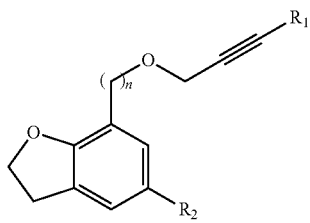

wherein n is 1,
R₁ is H or CH₃ and
R₂ is a linear (C₃-C₆)alkyl.

2. The compound of claim 1, wherein R₂ is n-butyl or n-hexyl.

3. The compound of claim 1, wherein the compound of Formula (I) is one of:
   5-n-hexyl -7-((prop-2-ynyloxy)methyl)-2,3-dihydrobenzofuran,
   5-n-hexyl-7-((but-2-ynyloxy)methyl)-2,3-dihydrobenzofuran,
   5-n-butyl-7-((but-2-ynyloxy)methyl)-2,3-dihydrobenzofuran,
   5-n-butyl-7-((prop-2-ynyloxy)methyl)-2,3-dihydrobenzofuran,
   5-n-propyl-7-((but-2-ynyloxy)methyl)-2,3-dihydrobenzofuran, and
   5-n-propyl-7-((prop-2-ynyloxy)methyl)-2,3-dihydrobenzofuran.

4. The compound of claim 3, wherein the compound is one of:
   5-n-hexyl-7-((prop-2-ynyloxy)methyl)-2,3-dihydrobenzofuran,
   5-n-hexyl-7-((but-2-ynyloxy)methyl)- 2,3-dihydrobenzofuran,
   5-n-butyl-7-((but-2-ynyloxy)methyl)-2,3-dihydrobenzofuran,
   5-n-butyl-7-((but-2-ynyloxy)methyl)- 2,3-dihydrobenzofuran, and
   5-n-propyl-7-((but-2-ynyloxy)methyl)-2,3-dihydrobenzofuran.

5. The compound of claim 4, wherein the compound is one of 5-n-butyl-7-((but-2-ynyloxy)methyl)-2,3-dihydrobenzofuran, and 5-n-propyl-7-((but-2-ynyloxy)methyl)-2,3-dihydrobenzofuran.

6. An insecticide composition comprising at least one insecticide active ingredient and at least one compound of Formula (I) according to claim 1 to insects directly and/or a biotope thereof.

7. An insecticide formulation comprising the insecticide composition of claim 6 and a carrier.

8. A non-therapeutic method for killing insects in closed and open environments, said method comprising the step of applying the insecticide composition of claim 6.

9. The method of claim 8 for killing insects in agriculture.

10. The method of claim 8, wherein the insects are selected from the order insect group consisting of Hemiptera, Diptera, Blattaria, Thysanoptera, Isoptera, and Acarina.

11. A therapeutic method for treating pediculosis in humans, said method comprising applying the insecticide composition of claim 6.

12. A therapeutic method for treating non-systemic or systemic parasites and insects in non-human mammals comprising applying the pesticide composition of claim 6 systemically or non-systemically to non-human mammals.

* * * * *